(12) United States Patent
Chen

(10) Patent No.: US 12,193,863 B2
(45) Date of Patent: Jan. 14, 2025

(54) X RAY IMAGE PROCESSING METHOD

(71) Applicant: InnoCare Optoelectronics Corporation, Tainan (TW)

(72) Inventor: Yu-Heing Chen, Tainan (TW)

(73) Assignee: InnoCare Optoelectronics Corporation, Tainan (TW)

(*) Notice: Subject to any disclaimer, the term of this patent is extended or adjusted under 35 U.S.C. 154(b) by 411 days.

(21) Appl. No.: 17/685,399

(22) Filed: Mar. 3, 2022

(65) Prior Publication Data

US 2022/0313194 A1    Oct. 6, 2022

(30) Foreign Application Priority Data

Mar. 31, 2021   (CN) .......................... 202110348522.0

(51) Int. Cl.
*A61B 6/00* (2024.01)
*A61B 6/46* (2024.01)
*G06T 7/00* (2017.01)

(52) U.S. Cl.
CPC ............ *A61B 6/5217* (2013.01); *A61B 6/461* (2013.01); *G06T 7/0012* (2013.01); *G06T 2207/10116* (2013.01); *G06T 2207/30061* (2013.01)

(58) Field of Classification Search
CPC ....... A61B 6/5217; A61B 6/461; A61B 6/467; A61B 6/468; A61B 6/469; A61B 6/563; A61B 6/566; A61B 6/42; A61B 6/4283; A61B 6/4405; A61B 6/4411; A61B 6/5205; A61B 6/5211; A61B 6/52; G06T 7/0012; G06T 2207/10116; G06T 2207/30061;

(Continued)

(56) References Cited

U.S. PATENT DOCUMENTS

2020/0334806 A1   10/2020  Hieda et al.
2021/0343054 A1*  11/2021  Wang .................... G06T 11/006

FOREIGN PATENT DOCUMENTS

CN    205229072 U  *  5/2016   ............. G01N 23/04
CN    108348172        7/2018

OTHER PUBLICATIONS

Tanaka, R., 2016. Dynamic chest radiography: flat-panel detector (FPD) based functional X-ray imaging. Radiological physics and technology, 9(2), pp. 139-153.*

(Continued)

*Primary Examiner* — Zhitong Chen
(74) *Attorney, Agent, or Firm* — JCIPRNET

(57) ABSTRACT

Provided is an X ray image processing method including the following. One of computing modules stored in an X ray device is activated, in which the one of the computing modules corresponds to a measurement area. The measurement area corresponding to the one of the computing modules is measured by an image measurement module, and a measurement signal is produced. The measurement signal is transmitted to a computing unit by the image measurement module. A measurement image is computed by the computing unit according to the measurement signal, and is stored in a first storage unit in the X ray device. The one of the computing modules is written to the computing unit. The measurement image is transmitted to the computing unit by the first storage unit. The measurement image is analyzed by the computing unit using the one of the computing modules, and an analysis image is generated.

19 Claims, 5 Drawing Sheets

(58) Field of Classification Search
CPC ............. G06T 7/10; G06T 2207/20081; G06T 2207/20084
See application file for complete search history.

(56) References Cited

OTHER PUBLICATIONS

Hata, A., Yamada, Y., Tanaka, R., Nishino, M., Hida, T., Hino, T., Ueyama, M., Yanagawa, M., Kamitani, T., Kurosaki, A. and Sanada, S., 2020. Dynamic Chest X-Ray Using a Flat-Panel Detector System: Technique and Applications. Korean Journal of Radiology, 22(4), pp. 634-651.*

* cited by examiner

X RAY IMAGE PROCESSING METHOD

CROSS-REFERENCE TO RELATED APPLICATION

This application claims the priority benefit of China application serial no. 202110348522.0, filed on Mar. 31, 2021. The entirety of the above-mentioned patent application is hereby incorporated by reference herein and made a part of this specification.

BACKGROUND

Technical Field

The disclosure generally relates to image processing, and, in particular, to an X ray image processing method.

Description of Related Art

Currently, when an X ray flat panel detector (FPD) obtains an X ray image, it needs to send the X ray image to a back end computer apparatus for analysis. In other words, instant X ray image processing is not available in the current X ray flat panel detector and a processing method thereof. Furthermore, if the computer apparatus is too old or bandwidth for data transmission is too small, a processing speed of the X ray image may be affected. In specific cases of application of X ray imaging such as passenger security screening at an airport or other transportation system, and an emergency room examination, in which an instant X ray image is required for detection of, for example, pneumonia or other chest lesions, the current apparatus and processing methods may not suit the needs. Accordingly, there have been awaited development of an X ray flat panel detector and an X ray image processing method that are capable of performing instant image analysis.

SUMMARY

The disclosure is directed to an X ray image processing method which generates an analysis image of an X ray image.

According to an embodiment of the disclosure, the X ray image processing method of the disclosure includes the following. One of multiple computing modules stored in an X ray device is activated, in which the one of the computing modules corresponds to a measurement area. The measurement area corresponding to the one of the computing modules is measured by an image measurement module, and a measurement signal is produced. The measurement signal is transmitted to a computing unit by the image measurement module. A measurement image is computed by the computing unit according to the measurement signal, and the measurement image is stored in a first storage unit of the X ray device. The one of the computing modules is written to the computing unit. The measurement image is transmitted to the computing unit by the first storage unit. The measurement image is analyzed by the computing unit using the one of the computing modules, and an analysis image is generated.

In light of the above, in the X ray image processing method of the disclosure, an X ray image is analyzed using a computing module corresponding to a specific measurement area, and a corresponding analysis image is generated.

Several exemplary embodiments accompanied with figures are described in detail below to further describe the disclosure in details.

DESCRIPTION OF THE EMBODIMENTS

Figure 1:
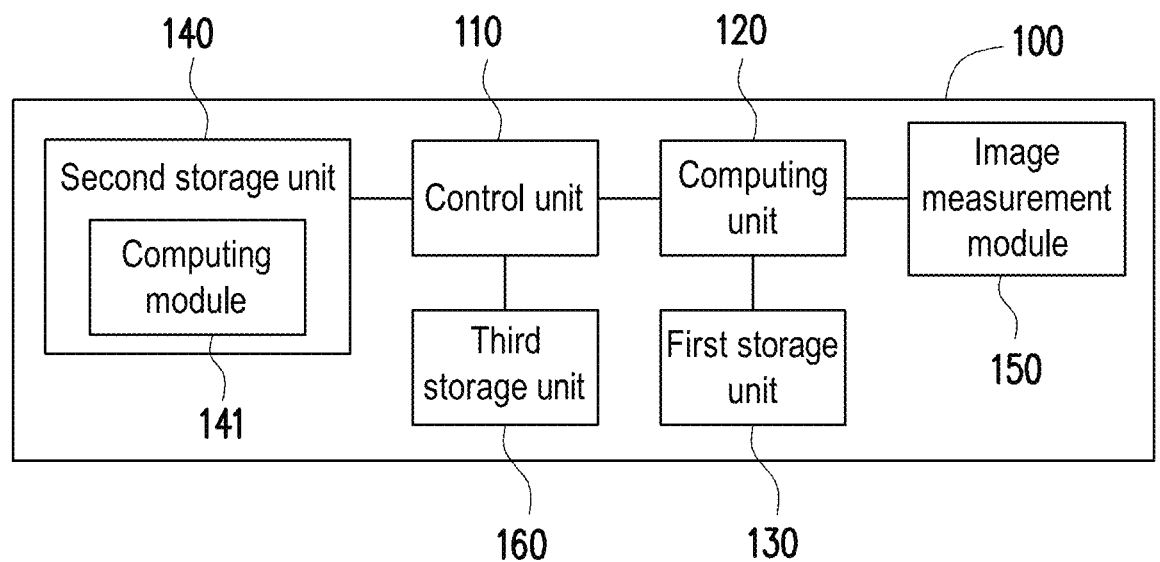
FIG. 1 is a schematic block diagram of an X ray device according to an embodiment of the disclosure.

Reference will now be made in detail to exemplary embodiments of the disclosure, examples of which are illustrated in the accompanying drawings. Wherever possible, the same reference numerals are used in the drawings and the description to refer to the same or like parts. Note that, to facilitate understanding and for simplicity of illustration, several of the drawings in the disclosure only illustrate a part of an electronic device or a display device, and some particular components are not illustrated based on their actual scale. In addition, the number and size of the elements shown in the drawings are exemplary and are not intended to limit the disclosure.

Throughout the description and the appended claims, certain terms are used to refer to specific elements. Those skilled in the art should understand that electronic apparatus manufacturers may refer to the same component by different terms. The present specification does not intend to distinguish between components that differ in name but not function. In the following description and the claims, the terms such as "comprise" and "include" are open-ended and should be interpreted as "include but not limited to."

In some embodiments of the disclosure, the terms related to joining and connecting, like "connect" and "interconnect", may mean a direct contact between two structures, or an indirect contact between two structures via an intervening structure, unless specifically defined. The terms related to joining and connecting may include the cases where both structures are removable or both structures are fixed. In addition, the terms "electrically connect" and "couple" include any direct and indirect electrical connection.

In the following embodiments, the same or similar elements are denoted with the same or similar reference numerals, and the same description will not be repeated. In addition, features of different embodiments may be arbitrarily mixed or combined as long as the mixture or combination does not violate the spirit of the disclosure or cause any contradiction. All simple equivalent changes and modifications made in accordance with the present specification or claims still fall within the scope of the disclosure. In the description or the claims, the terms such as "first" and "second" are used to name different elements or distinguish between different embodiments and ranges, instead of setting an upper/lower limit on the number of components or limiting a manufacturing order or disposition order of the elements.

Note that the features of the following embodiments may be replaced, rearranged, or mixed to complete other embodiments without departing from the spirit of the disclosure. The features of the embodiments may be arbitrarily mixed or combined as long as the mixture or combination does not violate the spirit of the disclosure or cause any contradiction.

FIG. 1 is a schematic block diagram of an X ray device according to an embodiment of the disclosure. Referring to FIG. 1, an X ray device 100 may be an X ray flat panel detector (FPD). In particular, the X ray device 100 in the disclosure is, for example, a digital radiography (DR) X ray system for remote backup. The X ray device 100 may be a mobile image capture device and may be used to obtain a measurement image (for example, an X ray image). The X ray device 100 includes a control unit 110, a computing unit 120, a first storage unit 130, a second storage unit 140, an image measurement module 150, and a third storage unit 160. In this embodiment, the control unit 110 is coupled to the computing unit 120, the second storage unit 140, and the third storage unit 160. The computing unit 120 is further coupled to the first storage unit 130 and the image measurement module 150. The control unit 110 is able to communicate with other electronic devices or electronic units to receive a control signal and/or output image data. In some embodiments of the disclosure, multiple computing modules 141 may be stored in the second storage unit 140 of the X ray device 100. In some embodiments, each of the computing modules 141 may correspond to a different measurement area (for example, a different human body part), or at least one of the computing modules 141 may correspond to multiple different measurement areas; however, the disclosure is not limited thereto. The computing module 141 may be a program, software, or other element which performs a computing function. In other embodiments of the disclosure, the X ray device 100 may not include the third storage unit 160.

In this embodiment, the control unit 110 may be a central processing unit (CPU) and may communicate with other electronic devices or electronic units through a wired or wireless communication module. For example, the control unit 110 may be connected to other electronic devices or electronic units through a connection wire or may communicate with other electronic devices or electronic units through Bluetooth or Wi-Fi. The computing unit 120 may be a field programmable gate array (FPGA), a graphics processing unit (GPU), or other appropriate element. The computing unit 120 may be used to receive and execute a module written by the control unit 110 and/or receive a measurement signal transmitted by the image measurement module 150 and generate a corresponding measurement image. In this embodiment, the image measurement module 150 may include a measurement instrument array that includes multiple measurement instruments for X ray measurement. When the image measurement module 150 performs measurement, a measurement target may be placed between an X ray light source and the image measurement module 150. The X ray light source may illuminate the measurement target, and the image measurement module 150 may produce the measurement signal and send the measurement signal to the computing unit 120.

In this embodiment, the first storage unit 130 and the third storage unit 160 may be the same type or different types of storages. The first storage unit 130 and the second storage unit 140 may be the same type or different types of storages. For example, the first storage unit 130 and the third storage unit 160 may be dynamic random access memories (DRAMs), and the first storage unit 130 and the third storage unit 160 may be the same memory or different memories that are separately disposed. The first storage unit 130 may be accessed by the computing unit 120, and may store the measurement image generated by the computing unit 120 according to the measurement signal and/or an analysis image generated by the computing unit 120 after analyzing the measurement image. In some embodiments, the first storage unit 130 may store a module written by the control unit 110. The third storage unit 160 may be accessed by the control unit 110 and may store the measurement image and/or the analysis image. The second storage unit 140 may be a flash memory. The second storage unit 140 may be accessed by the control unit 110 and may store one or more computing modules 141.

Figure 2:
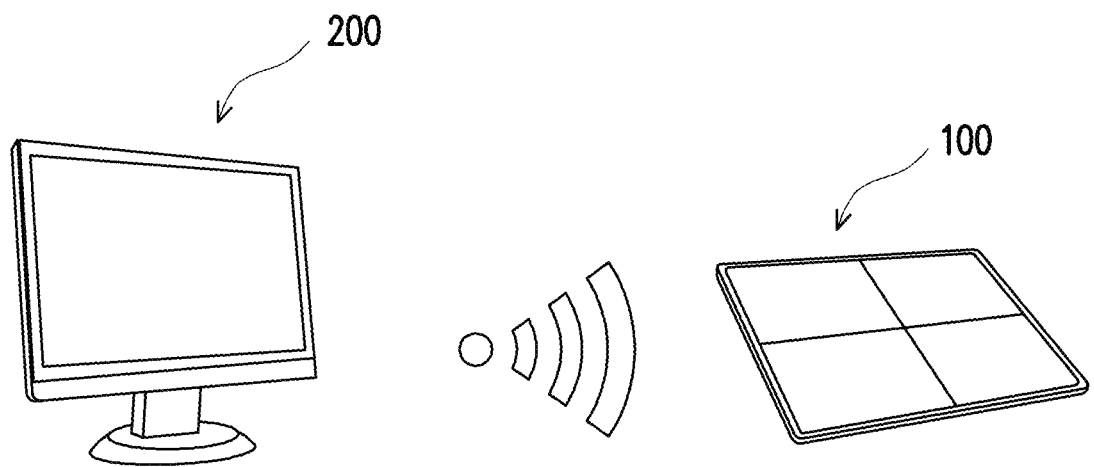
FIG. 2 is a schematic diagram illustrating communication between a master control device and a display device according to an embodiment of the disclosure.

FIG. 2 is a schematic diagram illustrating communication between a master control device and a display device according to an embodiment of the disclosure. Referring to FIG. 1 and FIG. 2, in this embodiment, the X ray device 100 may first be connected to (communicate with) to an electronic device 200, in which the electronic device 200 may be, for example, a personal computer (PC), a laptop, a tablet, or a smart phone. Also, the electronic device 200 may output a control signal to the X ray device 100 under user control or automatically. For example, when the user needs to measure and analyze an X ray image of a measurement area of a lung by the X ray device 100, the user may start up the X ray device 100 and connect it to the electronic device 200. The user may operate the electronic device 200 to make the electronic device 200 output a corresponding control signal to the X ray device 100, so as to set the X ray device 100 to execute a measurement module corresponding to the measurement area of the lung. For example, before the computing module 141 stored in the X ray device 100 is activated, the control unit 110 of the X ray device 100 receives the control signal. Next, the X ray device 100 and the electronic device 200 may stop connection therebetween, and the user may move the X ray device 100 to another place to perform image measurement. For example, the control signal may be provided by a device other than the X ray device 100 or may also be provided by a unit other than the control unit 110 disposed in the X ray device 100. The disclosure is not limited thereto.

In addition, in other embodiments of the disclosure, the X ray device 100 may be set to perform a function of measuring an X ray image. Also, the X ray device 100 may further display a current operation mode by a display screen or an indicator light disposed on a side surface of the X ray device 100. For example, when the X ray device 100 activates the above-mentioned function of analyzing the X ray image, the display screen or the indicator light may be in a first display state. When the X ray device 100 does not activate (or turns off) the above-mentioned function of analyzing the X ray image and performs the function of measuring the X ray image, the display screen or the indicator light may be in a second display state. Alternatively, when the X ray device 100 determines that the measurement image obtained includes the measurement area of the lung that corresponds to the settings, the display screen or the indicator light may be in a third display state. When the X ray device 100 determines that the measurement image obtained does not include the measurement area of the lung that corresponds to the settings, the display screen or the indicator light may be in a fourth display state. Therefore, the user may confirm the current operation mode of the X ray device 100 according to the display screen or the indicator light.

Figure 3:
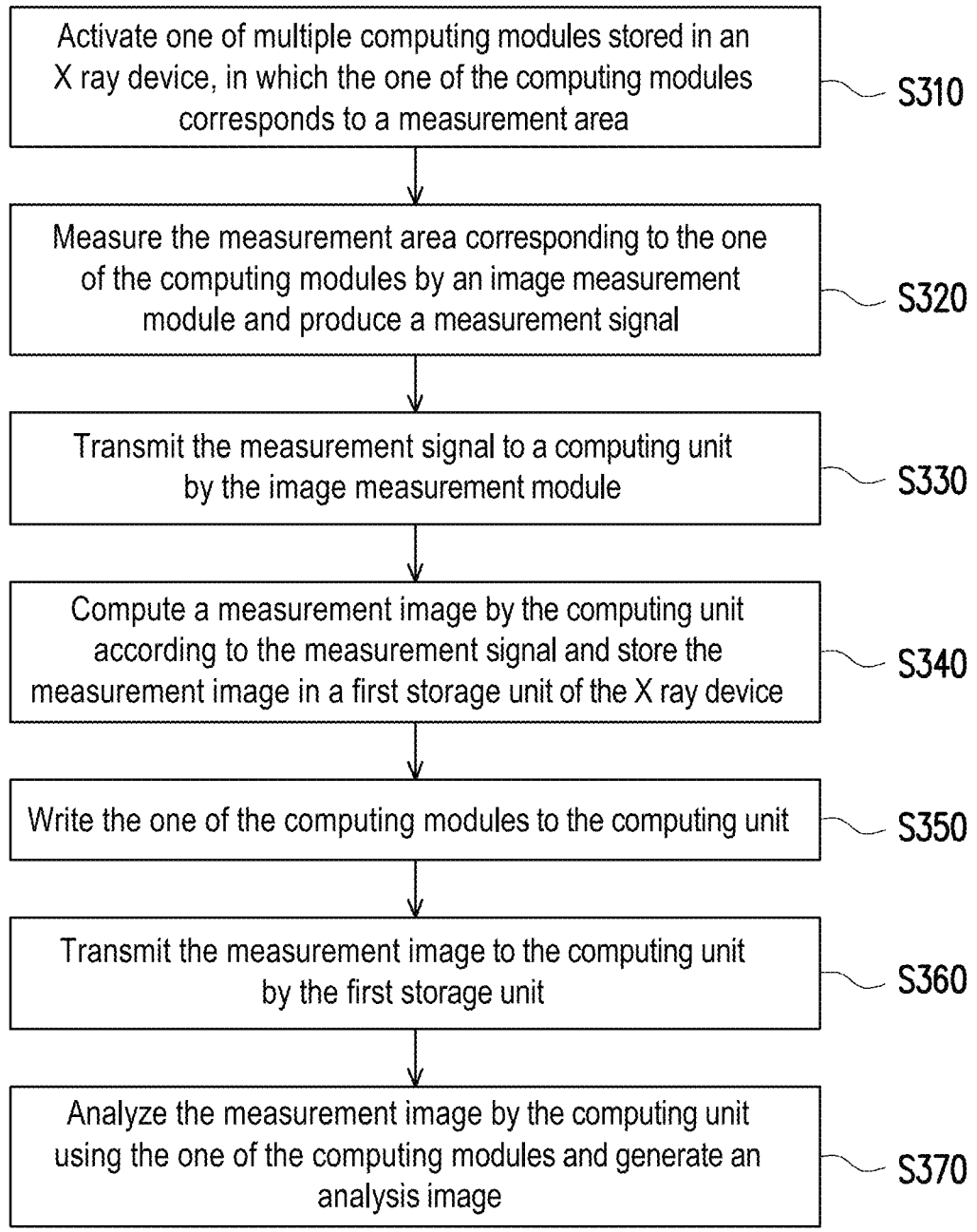
FIG. 3 is a flowchart of an X ray image processing method according to an embodiment of the disclosure.
Figure 4A:
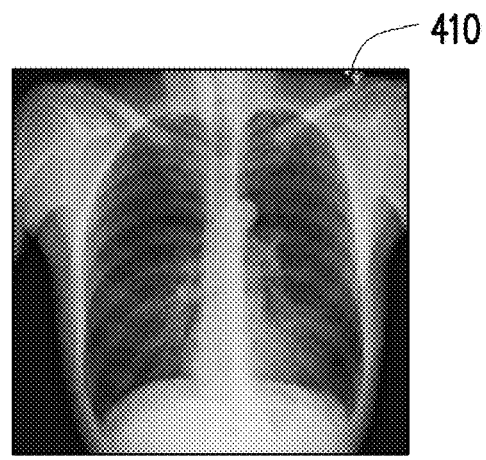
FIG. 4A is a schematic diagram of a measurement image according to an embodiment of the disclosure.

FIG. 3 is a flowchart of an X ray image processing method according to an embodiment of the disclosure. Referring to FIG. 1 to FIG. 3, after the X ray device 100 completes the operations as described in the embodiment of FIG. 2, the X ray device 100 may perform steps S310 to S370 illustrated in FIG. 3. In step S310, the control unit 110 may activate one of multiple computing modules stored in an X ray device according to a control signal, in which the one of the computing modules corresponds to a measurement area. Specifically, as shown in FIG. 1, the control unit 110 may activate the computing module 141 stored in the second storage unit 140 according to the control signal. The control unit 110 may first search for a position where the computing module 141 is stored in the second storage unit 140. In step S320, the measurement area corresponding to the one of the computing modules may be measured by the image measurement module 150, and a measurement signal may be produced. In step S330, the measurement signal may be transmitted to the computing unit 120 by the image measurement module 150. In step S340, a measurement image may be computed by the computing unit 120 according to the measurement signal, and the measurement image may be stored in the first storage unit 130 of the X ray device 100. Specifically, referring also to FIG. 4A, the image measurement module 150 may measure a measurement area corresponding to one of the computing modules 141 and produce a corresponding measurement signal. The image measurement module 150 may send the measurement signal to the computing unit 120. The computing unit 120 may compute a measurement image 410 according to the measurement signal and store the measurement image 410 in the first storage unit 130 of the X ray device 100.

Figure 4B:
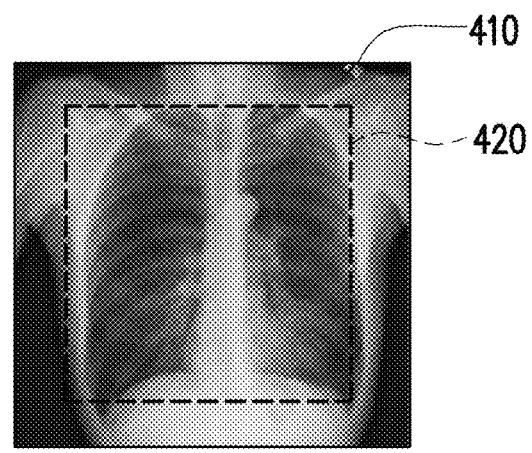
FIG. 4B is a schematic diagram of defining a measurement area in a measurement image according to an embodiment of the disclosure.
Figure 4C:
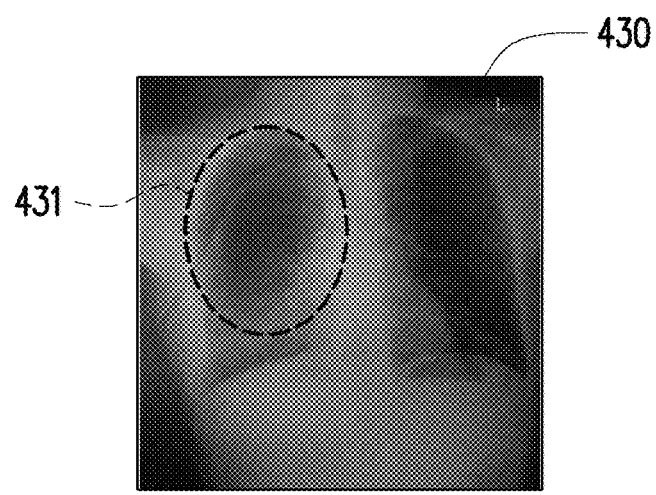
FIG. 4C is a schematic diagram of an analysis image according to an embodiment of the disclosure.

In step S350, the one of the computing modules is written to the computing unit 120. Specifically, as shown in FIG. 1, the control unit 110 may write the activated one of the computing modules 141 to the computing unit 120. In other words, when the computing unit 120 is to perform image analysis processing on the measurement image corresponding to a specific measurement area, since the control unit 110 has found the position where the computing module 141 is stored in the second storage unit 140, the computing module 141 may be written to the computing unit 120 to be executed. Next, in step S360, the measurement image may be transmitted to the computing unit 120 by the first storage unit 130. In step S370, the measurement image may be analyzed by the one of the computing modules 141, and an analysis image may be generated. Specifically, referring also to FIG. 4B and FIG. 4C, the first storage unit 130 may transmit the measurement image 410 stored therein to the computing unit 120, and the computing unit 120 may execute one of the computing modules 141 and analyze the measurement image 410. More specifically, the computing unit 120 may perform image analysis on a measurement area 420 in the measurement image 410.

Note that at least one of the computing modules 141 may include an algorithm, and the algorithm is for grayscale value calculation on the measurement image 410. The measurement area 420 may be an area corresponding to a lung area. The computing unit 120 may determine the measurement area 420 in the measurement image 410. After the computing unit 120 performs the image analysis on the measurement area 420 in the measurement image 410 by using the computing module 141, an analysis image 430 may be generated. The algorithm may include an artificial intelligence (AI) computation model, a neural network (NN) computation model, or a combination thereof, in which deep learning may be performed and an X ray image of a specific human body part may undergo image analysis and recognition through training. For example, the algorithm may include a U-Net deep learning segregation model or a similar semantic segmentation model. The computing unit 120 may first execute the model mentioned above and determine the measurement area 420 in the measurement image 410. The measurement image 410 may be a grayscale image, and the computing unit 120 may calculate a grayscale value of each pixel in the measurement image 410. In addition, the algorithm may further include, for example, a deep residual network (ResNet) model and/or a gradient-weighted class activation mapping (GRAD-CAM) model. The computing unit 120 may then execute, for example, the deep residual network model and determine an abnormal part 431 in the measurement area 420 and execute, for example, the gradient-weighted class activation mapping model and perform heatmap coloring to generate the analysis image 430. In other words, when the measurement area 420 of the measurement image 410 contains the abnormal part 431 such as, for example, an abnormal lung tissue change due to pneumonia, in some embodiments, a pixel in a position corresponding to the abnormal part 431 in the analysis image 430 may have a specific color distribution, thereby prompting the user or a medical professional to make a medical image diagnosis on the lung tissue corresponding to the position with the specific color distribution in the analysis image 430. In other embodiments, the position corresponding to the abnormal part 431 in the analysis image 430 may be shown in different grayscales for the user to make a medical image diagnosis.

In this embodiment, the measurement image 410 and/or the analysis image 430 generated by the computing unit 120 may be stored in the first storage unit 130 or the third storage unit 160. When the X ray device 100 and the display device are in connection, the control unit 110 may output the measurement image 410 and/or the analysis image 430 to the display device for display by accessing the first storage unit 130 or the third storage unit 160. Alternatively, in some embodiments of the disclosure, the X ray device 100 may include the display device that is able to display the measurement image 410 and/or the analysis image 430. Accordingly, in the X ray image processing method and/or the X ray device 100 of this embodiment, based on the measurement image 410, the corresponding analysis image 430 may be rapidly generated.

Figure 5:
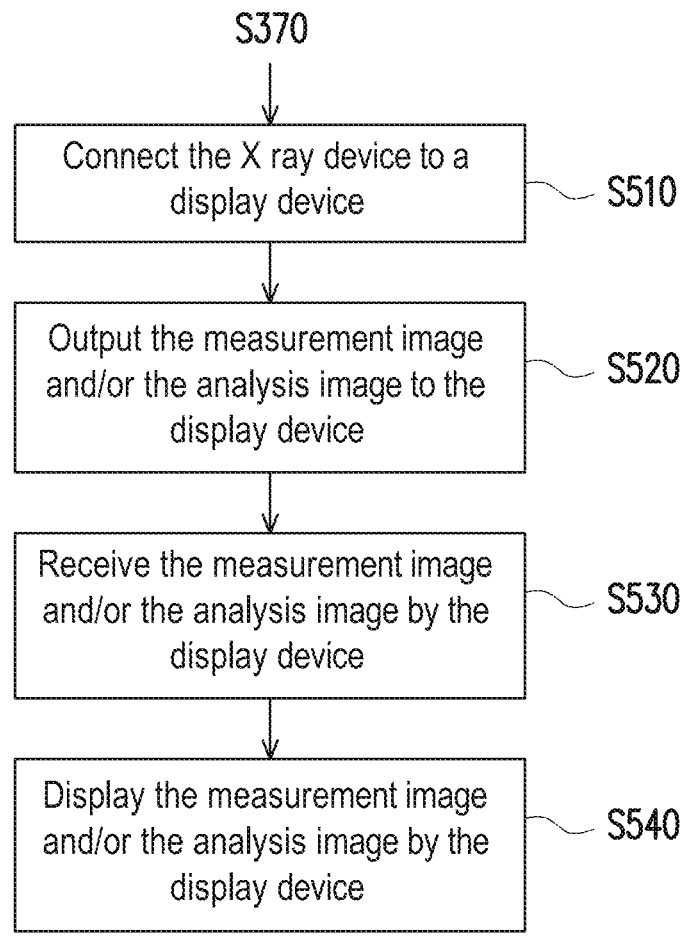
FIG. 5 is a flowchart of outputting a measurement image and an analysis image according to an embodiment of the disclosure.
Figure 6:
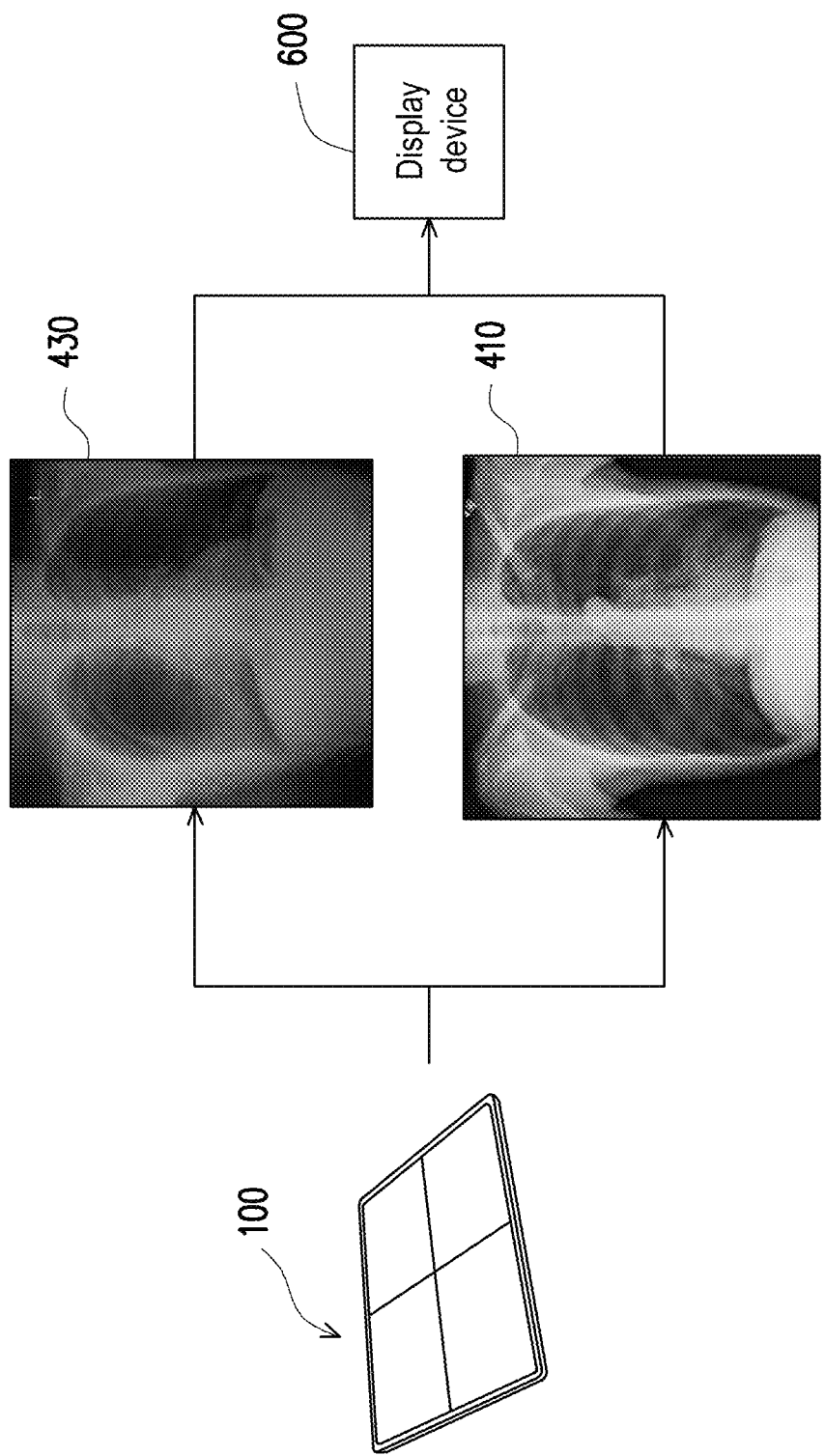
FIG. 6 is a schematic diagram of outputting a measurement image and an analysis image according to an embodiment of the disclosure.

FIG. 5 is a flowchart of outputting a measurement image and an analysis image according to an embodiment of the disclosure. FIG. 6 is a schematic diagram of outputting a measurement image and an analysis image according to an embodiment of the disclosure. Referring to FIG. 5 and FIG. 6, in some embodiments of the disclosure, after the X ray device 100 completes the image processing and/or analysis operations as described in the embodiment of FIG. 3, the X ray device 100 may subsequently perform steps S510 to S540. In step S510, the X ray device 100 may be connected to a display device 600. For example, the X ray device 100 may be connected to the display device 600 through a connection wire or through Bluetooth or Wi-Fi. However, the disclosure is not limited thereto. The display device 600 may be the electronic device 200 in FIG. 2 or a device that is different from the electronic device 200 in FIG. 2. In step S520, the measurement image 410 and/or the analysis image 430 are output to the display device 600. As shown in FIG. 6, after a computing unit of the X ray device 100 generates an analysis image, a control unit of the X ray device 100 may output the measurement image 410 and/or the analysis image 430 to the display device 600. In step S530, the measurement image 410 and/or the analysis image 430 may be received by the display device 600. In step S540, the measurement image 410 and/or the analysis image 430 may be displayed by the display device 600.

Accordingly, the X ray device 100 performs image analysis processing on the measurement image 410 before being connected to the display device 600, without a need for the display device 600 to additionally perform an operation related to image analysis processing. Therefore, after the X ray device 100 is connected to the display device 600, the user is able to quickly obtain an X ray measurement result and/or an X ray image analysis result corresponding to a specific measured part through the display device 600. From another point of view, the above-mentioned X ray image processing method may reduce hardware requirements of the display device 600.

In summary, in the X ray image processing method in the disclosure, a computing module corresponding to a specific measurement area may be executed to perform an instant image analysis on an obtained measurement image and a corresponding analysis image may be generated. In the X ray image processing method in the disclosure, the measurement image and/or the analysis image may be transmitted to the display device for display, and thus, the need for external communication and/or external image data processing during an X ray image processing process can be eliminated.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. An X ray image processing method, comprising:
    activating one of a plurality of computing modules stored in an X ray device, wherein the one of the plurality of computing modules corresponds to a measurement area;
    measuring the measurement area corresponding to the one of the plurality of computing modules by an image measurement module and producing a measurement signal;
    transmitting the measurement signal to a computing unit by the image measurement module;
    computing a measurement image by the computing unit according to the measurement signal and storing the measurement image in a first storage unit of the X ray device;
    writing the one of the plurality of computing modules to the computing unit;
    transmitting the measurement image to the computing unit by the first storage unit; and
    analyzing the measurement image by the computing unit using the one of the plurality of computing modules and generating an analysis image,
    wherein analyzing the measurement image by the computing unit using the one of the plurality of computing modules and generating the analysis image comprises:
        executing a U-Net deep learning segregation model or a similar semantic segmentation model by the computing unit to determine the measurement area in the measurement image;
        calculating a grayscale value of each pixel in the measurement image by the computing unit to execute a deep residual network model and determine an abnormal part in the measurement area; and
        executing a gradient-weighted class activation mapping model and performing heatmap coloring to generate the analysis image.

2. The X ray image processing method according to claim 1, comprising, after generating the analysis image by the computing unit, outputting the measurement image and the analysis image.

3. The X ray image processing method according to claim 2, further comprising:
    outputting the measurement image and the analysis image to a display device; and
    displaying the measurement image and the analysis image by the display device.

4. The X ray image processing method according to claim 1, wherein the plurality of computing modules are stored in a second storage unit of the X ray device.

5. The X ray image processing method according to claim 4, wherein the first storage unit and the second storage unit are different types of storages.

6. The X ray image processing method according to claim 4, wherein the second storage unit is a flash memory.

7. The X ray image processing method according to claim 1, wherein a control unit of the X ray device activates the one of the plurality of computing modules.

8. The X ray image processing method according to claim 1, comprising, before activating the one of the plurality of computing modules stored in the X ray device, receiving a control signal by a control unit of the X ray device.

9. The X ray image processing method according to claim 1, wherein the one of the plurality of computing modules comprises an algorithm, and the algorithm is for grayscale value calculation on the measurement image.

10. The X ray image processing method according to claim 1, wherein the measurement area corresponds to a lung area.

11. The X ray image processing method according to claim 1, wherein the X ray device is an X ray flat panel detector.

12. The X ray image processing method according to claim 1, wherein the first storage unit is a dynamic random access memory.

13. The X ray image processing method according to claim 1, further comprising:
    storing the measurement image in a third storage unit of the X ray device.

14. The X ray image processing method according to claim 13, wherein the third storage unit is a dynamic random access memory.

15. The X ray image processing method according to claim 1, further comprising:
    storing the analysis image in a third storage unit of the X ray device.

16. The X ray image processing method according to claim 1, wherein a pixel in a position corresponding to the abnormal part in the analysis image has a specific color distribution.

17. The X ray image processing method according to claim 1, wherein the measurement image is a grayscale image.

18. The X ray image processing method according to claim 1, wherein a pixel in a position corresponding to the abnormal part in the analysis image is shown in different grayscales.

19. The X ray image processing method according to claim 1, further comprising:
- displaying a current operation mode by a display screen or an indicator light disposed on a side surface of the X ray device.

* * * * *